United States Patent [19]

Rapkin et al.

[11] Patent Number: 6,096,270
[45] Date of Patent: Aug. 1, 2000

[54] APPARATUS AND METHODS USEFUL IN DETERMINING DISINFECTANT EFFECTIVE CONCENTRATION OF HYPOCHLORITE IONS

[75] Inventors: Myron Rapkin, Indianapolis, Ind.; David Tabb, Springfield, Ill.

[73] Assignee: Hapak Enterprises, Crawfordsville, Ind.

[21] Appl. No.: 09/071,908

[22] Filed: May 4, 1998

[51] Int. Cl.$^7$ .................................................... G01N 33/48
[52] U.S. Cl. ............................................. 422/61; 436/164
[58] Field of Search ................................ 422/58, 61, 28; 436/164, 174, 175

[56] References Cited

U.S. PATENT DOCUMENTS

| | | |
|---|---|---|
| 4,322,215 | 3/1982 | Huber et al. . |
| 4,339,243 | 7/1982 | Magers et al. . |
| 4,391,775 | 7/1983 | Huber et al. . |
| 4,578,245 | 3/1986 | Arai et al. ................................ 422/56 |
| 4,744,952 | 5/1988 | Ogita . |
| 4,938,926 | 7/1990 | Reiss . |
| 5,096,721 | 3/1992 | Levy . |
| 5,229,270 | 7/1993 | Ono et al. . |
| 5,300,442 | 4/1994 | Frant . |
| 5,491,094 | 2/1996 | Ramana et al. . |

*Primary Examiner*—Lyle A. Alexander
*Attorney, Agent, or Firm*—Fulbright & Jaworski, LLP

[57] ABSTRACT

The invention involves apparatus, reagents, and methods for determining a disinfecting effective amount of hypochlorite in a sample. These involve using enough neutralizing agent sufficient to neutralize up to, but no more, than 0.525%, or 5250 parts per million, of hypochlorite in a sample. If more than this amount is present in the sample, then an indicator system reacts with it to provide a detectable signal, such as color. If the hypochlorite is present at less than 0.525%, no signal forms. One can determine this in two minutes or less.

16 Claims, No Drawings

APPARATUS AND METHODS USEFUL IN DETERMINING DISINFECTANT EFFECTIVE CONCENTRATION OF HYPOCHLORITE IONS

FIELD OF THE INVENTION

This invention relates to reagents and apparatus useful in analyses of samples. In particular, it relates to such reagents and apparatus for determination of disinfectant effective amounts of sodium hypochlorite (bleach), in samples.

BACKGROUND AND PRIOR ART

Sodium hypochlorite (NaOCl) sometimes referred to as "household bleach", or, simply "bleach", is a standard disinfectant and biocidal agent, used in the home, and in industry, such as medical settings.

In solution, the sodium hypochlorite dissolves, forming, inter alia, the hypochlorite, or "OCl" ion. It is this hypochlorite ion which is the disinfecting or biocidal agent. The wide availability and low cost of NaOCl, as well as its ready solubility, have made it one of, if not the, preferred disinfecting/biocidal agent, especially in industry. Its efficacy has been studied, and as a result, regulatory and quasi-regulatory authorities have determined that a minimum concentration of 0.525%, or 5250 parts per million ("ppm"), of NaOCl, is necessary to meet disinfecting standards. Any solution with a strength less than this is not considered to meet required standards.

While it may, at first glance, seem easy to meet the minimal standards provided supra, there are issues with preparing these solutions. First, sodium hypochlorite is also an irritant, and can be toxic. "Chlorine eyes", the phenomenon of eye irritation from a swimming pool with a chlorine concentration that is too high, is one example of the irritation caused by concentrations which are too high. Further, it is simply not economical to prepare solutions where the concentration of the active ingredient is too high. As a result, there is a risk, when working with low concentrations of active material to dilute these to a point where required standards are not met.

Perhaps the most problematic issue in this area, however, is the aging of hypochlorite solutions. It is standard practice to prepare a large quantity of a bleach solution at a point in time and then to use it, on an as needed basis, rather than to prepare it when needed. This solution preparation can take place hours, or days, before the bleach is actually used. Sodium hypochlorite is less stable than water, and decomposes As a result, a solution which may contain a disinfectant/biocidal effective amount of hypochlorite when it is prepared may very well be below this standard at the point in time when it is used. Use of such solution fails to comply with sanitary guidelines, and may not result in effective disinfection of the material it is used upon.

There is a substantial body of literature in the determination of hypochlorite, and free chlorine, in samples. At the start, it must be noted that terminology in this field is not uniform, and it is not always clear as to what chlorine containing ion a particular reference is addressing. For purposes of this disclosure, hypochlorite is the OCl⁻ radical, and is the only determinant under consideration This is sometimes referred to as free chlorine or available chlorine in the relevant literature. U.S. Pat. Nos. 4,322,215 and 4,391,775 to Huber et al., are related as parent and divisional of each other. These references explain how it is important to distinguish between different species of chlorine in, e.g., drinking water. Hypochlorite it is explained, reacts with hydrogen peroxide, in a reaction which eventually yields free hydrogen, oxygen, and a chloride ion. This reaction, while of potential value in a completely liquid system, is not relevant to the invention described herein, for reasons which will be explained infra. In brief, hydrogen peroxide is unstable, and deteriorates upon standing. Hence, it is ineffective as a material needed to be impregnated into an analytical device, or used in a storage stable solution.

U.S. Pat. No. 5,491,094 to Ramana et al, discusses test strips which can be used in determining free chlorine in solutions. the patent discusses how chloramine, which is frequently present in solutions which also contain free chlorine, can interfere with the determination of the relevant analyte. As a result, Ramana et al. "buffer" their strips at high pH, i.e., 10 or more.

U.S. Pat. No. 5,300,442 to Frant discusses the reaction of chlorine with iodine, leading to iodide ions. In order to prevent iodide, which is determinable, from reverting back to iodine, which is not, zinc dust is added to the solution.

U.S. Pat. No. 5,229,270 to Ono shows a complex, enzyme activating reaction, to determine chlorine in solution. Such a system is not practical for the type of systems contemplated herein, and is not useful on a day to day basis.

U.S. Pat. No. 5,096,721 to Levy teaches that sodium thiosulfate can react with and inactivate free chlorine. The thiosulfate is added to the lining of a paper cup, so that when water is added thereto, any free chlorine is inactivated. This is not an analytical device of the type described herein, however.

U.S. Pat. No. 4,092,115 to Rupe teaches detection of free chlorine ions in a sample via the use of particular indicators. This is not unlike U.S. Pat. No. 5,155,048 to Williams et al., which teaches various aminoalkyl/alkyl ring containing indicators which are useful in determining chlorine in solution. An older patent, i.e., U.S. Pat. No. 3,937,613 to Rosicky, teaches immersion of test strips into a swimming pool, after which reagents disperse therein. If the pool water turns pink, then chlorine is present. Intensity of the pink color is used as a determination of how much free chlorine is present.

What is absent from any of these references is a teaching or suggestion of a "cutoff" determination system, i.e., one which only detects the analyte of interest, hypochlorite, if the analyte is present at a sufficiently high concentration, i.e., one that meets standards for disinfection. As defined herein, this is a concentration of at least 0.525%, or 5250 ppm. Determining that hypochlorite is present per se is not particularly useful in the situations described herein because, as noted supra, at concentrations below the defined minimum, the required disinfecting/biocidal properties of hypochlorite cannot be assured. Further, many of the systems described in the references simply are not economical, or practical, for day to day industrial or home use. Essentially, the invention involves apparatus and reagents which can be used simply, efficiently, and provides an answer to the question of whether or not minimum effective concentrations of hypochlorite are present, in two minutes or less. In the case of the apparatus of the invention, such as test strips, these are dry materials which can be used, e.g., by placing one or a few drops of the test solution thereon, and then reading the test strips in less than two minutes. In the reagent compositions of the invention, the same approach can be taken, i.e., the solution to be tested is combined with the reagent, and color formation is determined, against a neutral background such as white paper, in two minutes or less.

The inventive aspects and preferred features of the invention will be seen in the detailed description of the invention which follows.

DETAILED DESCRIPTION OF PREFERRED EMBODIMENTS

The invention is an apparatus useful in determining a disinfecting/biocidally effective concentration of hypochlorite in a sample. The apparatus contains, impregnated therein, a hypochlorite neutralizing reagent in an amount sufficient only to neutralize up to 0.525% hypochlorite in the test sample. Also impregnated in the apparatus is an indicator system which reacts with any remaining hypochlorite in the solution, to form a detectable signal, such as a color. The hypochlorite neutralizing agent and indicator system are impregnated into an absorbent carrier material, such as cellulose based papers, e.g. alpha cellulose paper, a fleece, or any other absorbent material. Optional materials include color stabilizing agents, color enhancers, preservatives, and so forth. Additionally, the absorbent material can be, but need not be, attached to a solid support, such as a plastic dipstick base of the type known in the art. Relevant dipstick type structures may be seen in, e.g., Ramana et al., U.S. Pat. No. 5,491,094 Ogita, U.S. Pat. No. 4,744,952 and Rupe et al., U.S. Pat. No. 4,092,115, all of which are incorporated by reference. It is to be understood that there are many alternate apparatus configurations which can be used, as long at the features described supra as essential, i.e., the neutralizing agent and the indicator system are present.

Also a part of the invention are compositions containing the materials listed supra. As will be seen from the examples described herein, the neutralizing agent and the indicator system are combined, to form an impregnating solution which is then used to impregnate the absorbent material. These reaction solutions, as well as mixtures of the reactants, in dry form, are also a part of the invention.

Also a part of the invention are methods for determining whether or not a disinfecting/biocidally effective amount of hypochlorite is present in the sample of interest, by contacting the apparatus with test sample, and then determining whether or not color forms, in a time period of two minutes or less.

The hypochlorite neutralizing agent may be any material which reacts with hypochlorite to neutralize it. There are many materials which can perform this function, including reductants, such as sodium thiosulfate, reducing sugars, ascorbic acid, and so forth, and antioxidants, such as propyl gallate, BHA, BHT, and so forth. Sodium thiosulfate is the preferred neutralizing agent. Whatever the neutralizing agent is, this should be present in an amount sufficient to neutralize up to 0.525% of sodium hypochlorite in a given sample. The amount of neutralizing agent necessary can be determined experimentally, or via reference to standards relating to redox potentials. For example, for sodium thiosulfate, a concentration of from about 9.95 to about 10.05% (weight/volume), or 0.16M will neutralize the requisite amount of hypochlorite. The amount of different neutralizing agents needed will vary, but as indicated supra, this is easily determinable. More specifically, the sodium thiosulfate concentration used is 0.16M. To determine the approximate appropriate amount of any other neutralizing agent, multiply its molecular weight by 0.16.

The indicator system may be any of the standard indicator systems known and used for determining anions in a sample. Exemplary of these indicator systems are Trinder reagent systems, such as combinations of 4-amino antipyrine and MAOS (N-ethyl-N- (2-hydroxy-3-sulfopropyl)-3,5-dimethylaniline), MOPS (4-morpholine propane sulfonic acid), 3,5,DCHBS (3,5-dichloro-2-hydroxy-benzenesulfonic acid) or TOOS (N-ethyl-N-2-hydroxy-3-sulfopropyl-m-toluidine), 3,3',5,5' tetramethylbenzidine, iodometric indicators, such as KI and KI/starch complexes, and so forth. See, e.g., Welcher, Chemical Solutions: Reagents Useful To The Chemist, Biologist and Bacteriologist (D. Van Nostrand Company, 1942), "Chlorine", for a listing of representative reagents, as well as the U.S. Patents cited supra, which teach additional systems.

Unlike the neutralizing agent discussed supra, the amount of indicator system used is not of critical importance.

Optional ingredient include color stabilizers or enhancers, such as polyethylene glycol, alginate, or carrageenan. Preservatives may also be used, as may enhancers/stabilizers, as optional items.

In practice, the apparatus of the invention is provided with instructions to the user which include, inter alia, the standard advice to read the test device in less than two minutes. This is standard in the area of diagnostic test strips. During this short time period, the neutralizing agent acts to eliminate reactive hypochlorite in the sample, so that it cannot react with the indicator system. If there is less than about 0.525% sodium hypochlorite in the sample, then there will be none left to react with the indicator, and there will be no relevant signal, such as appropriate intensity of color, on the test strip. This indicates that the solution of hypochlorite is not suitable for its intended use, and should either be discarded or reformulated by addition of more hypochlorite. On the other hand, if the apparatus provides sufficient intensity of a color, then the solution satisfies minimum requirements for use as a disinfectant/biocide.

In practice, it is preferred that an apparatus in accordance with the invention be used, where one or few drops of the test solution are contacted to the strip. Alternatively, the strip can be dipped into the solution, removed quickly, and read over a period of two minutes or less. Similarly, one can combine a solution of the reagent of the invention with a few drops of the test solution, optionally shake them together, and read the signal, e.g., color, or lack thereof, against a white background.

The color which is read may be measured against one of many standard systems which provide names or values for different intensities of color. In the examples which follow, the "Pantone Matching System" is used, but the choice of system and the values given are for the sake of completeness. In practice, the investigator will simply determine whether the strip or solution forms a color keyed to an appropriate reference standard.

The examples which follow should be considered as exemplary, and by no means limitative of the invention.

EXAMPLE 1

A formulation was prepared which contained 10% weight/volume ("w/v" hereafter) of sodium thiosulfate (4.0 ml), 10% w/v of 4-aminoantipyrine, (2.5 ml), 10% w/v MAOS (2.5 ml) 1% w/v polyethyleneglycol (PEG 8M; 0.25 ml), and 0.75 ml of distilled water. The formulation was applied to a bibulous cellulose matrix, dried, and the resulting dried paper was attached to double sided adhesive, and cut into ¼ inch wide ribbons. Then, release liner was removed from the paper, and the ribbon was placed onto white plastic. This material was then cut into ¼ inch wide reagent strips.

Hypochlorite solutions with known concentrations were prepared, and the test strips prepared supra were dipped into the solutions, and color development was measured in less than two minutes.

At 0.525%, a distinct peach color developed. The intensity of color increased, to deep pink, at 0.575%, and deep red at 1.05%. The colors listed herein are by reference to the Pantone Matching System.

EXAMPLE 2

A second group of test strips were prepared, by combining 4.2 ml sodium thiosulfate (10% w/v in $H_2O$), 2.5 ml 4-aminoantipyrine (10% in MeOH), 1.7 ml 3,5 DCHBS (100% in methoxyethanol), and 1.6 ml of distilled water. A second variety of bibulous paper was impregnated with the solution, and the resulting material was treated, and tested as described supra. The resulting color development was akin to that in example 1, using the same hypochlorite solutions.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An apparatus useful in determining presence of a disinfecting effective amount of sodium hypochlorite in a sample, comprising an absorbent carrier material having impregnated thereon:

(i) an amount of a hypochlorite neutralizing agent effective to neutralize a hypochlorite solution of 0.525%, and (ii) an indicator system reactive with any hypochlorite ion not neutralized by (i).

2. The apparatus of claim 1, wherein said indicator system is a Trinder reagent.

3. The apparatus of claim 1, wherein said indictor system comprises 4-amino antipyrene.

4. The apparatus of claim 1, wherein said indicator system comprises N-ethyl-N-(2-hydroxy-3-sulfopropyl)-3,5-dimethylaniline (MAOS).

5. The apparatus of claim 1, wherein said indicator system comprises 3,5-dichloro-2-hydroxy-benzenesulfonic acid (3,5 DCHBS).

6. The apparatus of claim 1, further comprising a color enhancer, a color stabilizer, or a preservative.

7. The apparatus of claim 1, further comprising a solid backing material to which said absorbent carrier material is attached.

8. The apparatus of claim 1, wherein said absorbent carrier material is a cellulose based paper.

9. The apparatus of claim 1, wherein said hypochlorite neutralizing agent is present at a concentration of approximately 0.16M of its molecular weight.

10. The apparatus of claim 1, wherein said neutralizing agent is a reducing sugar, ascorbic acid, propyl gallate, BHA or BHT.

11. The apparatus of claim 1, wherein said neutralizing agent is sodium thiosulfate.

12. The apparatus of claim 11, wherein said sodium thiosulfate is present at a concentration of about 0.16 M.

13. A method for determining whether a sample contains a disinfecting effective concentration of hypochlorite, comprising contacting the apparatus of claim 1 to said sample, and determining if a detectable signal forms in two minutes or less, formation of a detectable signal being indicative of a disinfecting effective amount of hypochlorite in said sample.

14. The method of claim 13, wherein said neutralizing agent is sodium thiosulfate.

15. The method of claim 13, wherein said indicator system is a Trinder reagent.

16. The method of claim 13, wherein said neutralizing agent is a reducing sugar, ascorbic acid, propyl gallate, BHA or BHT.

* * * * *